US012558024B2

(12) United States Patent
Heo et al.

(10) Patent No.: US 12,558,024 B2
(45) Date of Patent: Feb. 24, 2026

(54) SKIN DISEASE DETECTION SYSTEM AND SKIN DISEASE MANAGEMENT METHOD USING PORTABLE TERMINAL

(71) Applicant: AIFORPET, Pohang-si (KR)

(72) Inventors: Euna Heo, Seoul (KR); Eunsim Heo, Seoul (KR); Eundong Shin, Seoul (KR)

(73) Assignee: AIFORPET, Pohang-si (KR)

( * ) Notice: Subject to any disclaimer, the term of this patent is extended or adjusted under 35 U.S.C. 154(b) by 317 days.

(21) Appl. No.: 18/019,798

(22) PCT Filed: Oct. 30, 2020

(86) PCT No.: PCT/KR2020/015009
§ 371 (c)(1),
(2) Date: Feb. 4, 2023

(87) PCT Pub. No.: WO2022/030685
PCT Pub. Date: Feb. 10, 2022

(65) Prior Publication Data
US 2023/0301582 A1 Sep. 28, 2023

(30) Foreign Application Priority Data
Aug. 7, 2020 (KR) ........................ 10-2020-0099374

(51) Int. Cl.
*A61B 5/00* (2006.01)
*G16H 50/30* (2018.01)

(52) U.S. Cl.
CPC ........... *A61B 5/441* (2013.01); *A61B 5/0077* (2013.01); *A61B 5/4842* (2013.01); *A61B 5/6898* (2013.01); *G16H 50/30* (2018.01); *A61B 2503/40* (2013.01)

(58) Field of Classification Search
None
See application file for complete search history.

(56) References Cited

FOREIGN PATENT DOCUMENTS

| | | | | |
|---|---|---|---|---|
| CN | 110752025 A | * | 2/2020 | |
| JP | 2004303067 A | * | 10/2004 | |
| JP | 2020-102249 A | | 7/2020 | |
| KR | 10-2003-0032088 | | 4/2003 | |
| KR | 10-1602149 | | 3/2016 | |

(Continued)

OTHER PUBLICATIONS

English translation of JP-2004303067-A. (Year: 2004).*

(Continued)

*Primary Examiner* — Thomas D Lee
(74) *Attorney, Agent, or Firm* — ZION IP; Byungwoong Park

(57) ABSTRACT

Provided are a skin disease detection system and a skin disease management method using a portable terminal. The method comprises: generating, by a health management server, skin health standard data by matching basic skin condition information with basic skin result data; receiving, by the health management server, skin condition measurement information for a skin disease of a test subject from a user terminal; and generating, by the health management server, health result data by comparing and analyzing the skin condition measurement information on the basis of the skin health standard data.

11 Claims, 9 Drawing Sheets

| USER TERMINAL(10) | SERVICE LINK TERMINAL(30) | HEALTHCARE SERVER(20) |
|---|---|---|
| IMAGING UNIT(100) | | COMMUNICATION UNIT(200) |
| TRANSCEIVER UNIT(110) | | DATABASE UNIT(210) |
| MEMORY UNIT(120) | | MONITORING UNIT(220) |
| DISPLAY UNIT(130) | MANAGER TERMINAL(40) | DISEASE DATA MANAGEMENT UNIT(230) |
| TERMINAL CONTROL UNIT(140) | | TREATMENT DATA MANAGEMENT UNIT(240) |
| | | MANAGEMENT CONTROL UNIT(250) |

1000

(56)         References Cited

FOREIGN PATENT DOCUMENTS

| | | | |
|---|---|---|---|
| KR | 10-1863182 | 7/2018 | |
| KR | 10-2018-0135338 | 12/2018 | |
| KR | 2019070432 A * | 6/2019 | ........... A61B 5/7264 |
| WO | WO-2021141187 A1 * | 7/2021 | |

OTHER PUBLICATIONS

English translation of KR-2019070432-A. (Year: 2019).*
English translation of CN-110752025-A. (Year: 2020).*
English translation of WO-2021141187-A1 (Year: 2021).*
English Specification of 10-2003-0032088.
English Specification of JP2020-102249A.
English Specification of 10-2018-0135338.
English Specification of 10-1602149.
English Specification of 10-1863182.

* cited by examiner

1000

1000

1022

1020

102

( a )

1024

1022

( b )

AVERAGE R DISTRIBUTION DIAGRAM

AREA DISTRIBUTION DIAGRAM

DISTRIBUTION DIAGRAM OF EXTRACTED
WRINKLES AND WHITE SPOTS

FIG. 7

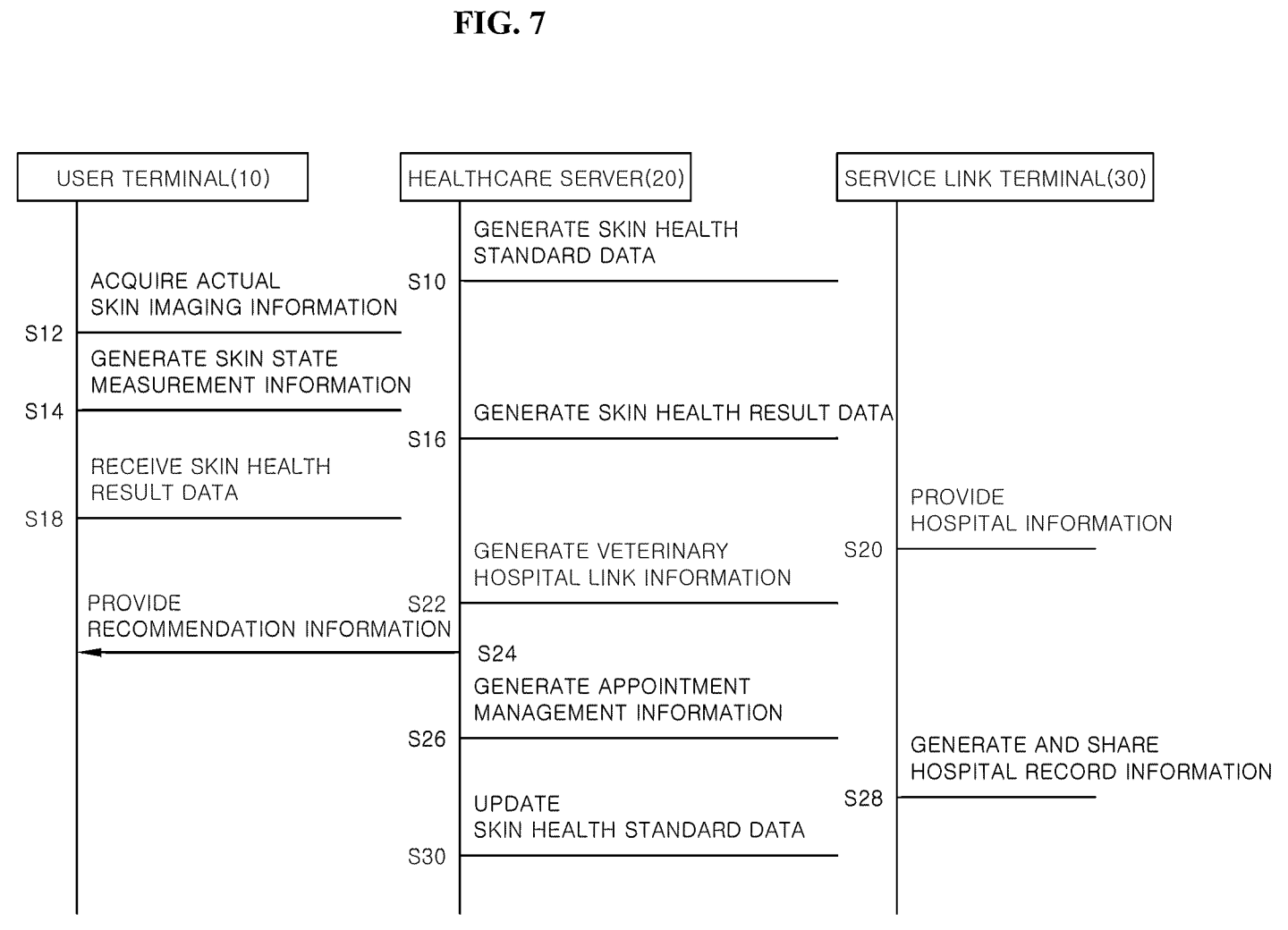

| USER TERMINAL(10) | HEALTHCARE SERVER(20) | SERVICE LINK TERMINAL(30) |
|---|---|---|

S10 — GENERATE SKIN HEALTH STANDARD DATA

S12 — ACQUIRE ACTUAL SKIN IMAGING INFORMATION

S14 — GENERATE SKIN STATE MEASUREMENT INFORMATION

S16 — GENERATE SKIN HEALTH RESULT DATA

S18 — RECEIVE SKIN HEALTH RESULT DATA

S20 — PROVIDE HOSPITAL INFORMATION

S22 — GENERATE VETERINARY HOSPITAL LINK INFORMATION

S24 — PROVIDE RECOMMENDATION INFORMATION

S26 — GENERATE APPOINTMENT MANAGEMENT INFORMATION

S28 — GENERATE AND SHARE HOSPITAL RECORD INFORMATION

S30 — UPDATE SKIN HEALTH STANDARD DATA

SKIN DISEASE DETECTION SYSTEM AND SKIN DISEASE MANAGEMENT METHOD USING PORTABLE TERMINAL

BACKGROUND OF THE INVENTION

Technical Field

The present invention relates to a skin disease measurement system and a skin disease management method using a portable terminal, that is, a skin disease measurement system and a skin disease management method using a portable terminal for quickly determining whether the skin of a test subject has a disease and quickly treating the test subject at an early stage.

Background Art

With the aging population structure and the increasing number of single households, human beings are gradually becoming self-centered and desolate. Accordingly, the number of people who recognize pets as family members or companions is increasing, and the companion animal market is also steadily growing.

When these companion animals have abnormal symptoms that are not usually seen, most of the companion animals are taken to a veterinary hospital for treatment, or the abnormal symptoms that occur in the companion animals are resolved on the basis of information obtained from nearby people or through the Internet, phone calls, etc.

However, information obtained from nearby people or through the Internet, phone calls, etc. is incorrect in many cases, and thus treatment may be difficult. Also, when people personally visit hospitals, there are many cases in which the waiting time at the hospital is long and the service is not properly provided to the customers due to the heavy hospital workload.

DETAILED DESCRIPTION OF THE INVENTION

Technical Problems

The present invention is directed to providing a skin disease measurement system and a skin disease management method using a portable terminal.

Objectives of the present invention are not limited to that described above, and other objectives which have not been described will be clearly understood by those of ordinary skill in the art from the following description.

Technical Solution

One aspect of the present invention provides a skin disease measurement method using a portable terminal, the skin disease measurement method including matching, by a healthcare server, basic skin state information with basic skin result data to generate skin health standard data, receiving, by the healthcare server, skin state measurement information for a skin disease of a test subject from a user terminal, and comparing and analyzing, by the healthcare server, the skin state measurement information on the basis of the skin health standard data to generate skin health result data. The generation of the skin health standard data includes preprocessing images included in basic skin imaging information included in the basic skin state information, extracting part-specific analysis images from the preprocessed images, analyzing and assessing a characteristic distribution diagram from the part-specific analysis images, and quantifying severity of the skin disease of the test subject using the analyzed characteristic distribution diagram.

The analyzing of the characteristic distribution diagram may include analyzing, by the healthcare server, a characteristic distribution diagram for at least one skin disease among erythema, excoriation, and lichenification from the part-specific analysis images using a multiple-residual concatenation (MRC) algorithm.

The healthcare server may assess severity of erythema using an average red (R) distribution diagram calculated from the part-specific analysis images, assess severity of excoriation using a distribution diagram of ratios of an area of wounded parts to a total area calculated from the part-specific analysis images, and severity of lichenification using a distribution diagram of the number of extracted wrinkles and white spots calculated from the part-specific analysis images.

The generation of the skin health standard data may include repeatedly learning, by the healthcare server, the basic skin result data corresponding to the basic skin state information to verify the basic skin result data.

The generation of the skin health result data may include extracting, by the healthcare server, part-specific actual analysis images from actual skin imaging information included in the skin state measurement information and correcting the part-specific actual analysis images, analyzing, by the healthcare server, a characteristic distribution diagram from the part-specific actual analysis images, and comparing and analyzing, by the healthcare server, the characteristic distribution diagram and the skin health standard data and quantifying and assessing severity of the skin disease of the test subject to generate the skin health result data.

The skin disease measurement method may include transmitting or receiving, by the healthcare server, treatment management data generated in accordance with the skin health result data to or from the user terminal.

The skin disease measurement method may include transmitting and receiving, by the healthcare server, the treatment management data between the user terminal and a service link terminal.

The skin disease measurement method may further include updating, by the healthcare server, the skin health standard data in real time in accordance with the skin health result data.

Another aspect of the present invention provides a skin disease management method using a portable terminal, the skin disease management method including generating, by a healthcare server, skin healthcare data corresponding to skin state measurement information for a skin disease of a test subject received from a user terminal, sharing, by the healthcare server, the skin healthcare data with a service link terminal, transmitting, by the healthcare server, recommendation information generated in accordance with the skin healthcare data on the basis of hospital information received from the service link terminal to the user terminal, transmitting and receiving, by the healthcare server, appointment management information between the user terminal and the service link terminal, and generating, by the service link terminal, treatment management data in accordance with the skin health result data. The service link terminal periodically transmits notification information about the test subject to the user terminal.

Another aspect of the present invention provides a skin disease measurement system using a portable terminal, the skin disease measurement system including a user terminal configured to generate skin state measurement information including actual skin imaging information of a skin disease acquired from a test subject and a healthcare server configured to learn skin health standard data generated by matching basic skin state information with basic skin result data, analyze the skin state measurement information, quantify severity of the skin disease of the test subject, and generate skin health result data. The healthcare server generates the skin health result data by analyzing a characteristic distribution diagram for at least one skin disease among erythema, excoriation, and lichenification using part-specific analysis images extracted from the actual skin imaging information.

The skin disease measurement system may include a service link terminal configured to share treatment management data generated in accordance with the skin health result data.

The skin disease measurement system may further include a manager terminal configured to receive the skin state measurement information from the user terminal, repeatedly learn the skin health standard data when the skin health standard data is received from the healthcare server, and generate the skin health result data corresponding to the skin state measurement information.

Another aspect of the present invention provides a program stored in a computer-readable recording medium to perform the skin disease measurement method using a portable terminal and the skin disease management method using a portable terminal in combination with a computer which is hardware.

Other details of the present invention are included in the detailed description and drawings.

Advantageous Effects

According to the present invention, when an abnormality occurs in the skin of a test target, particularly, a companion animal, a current state of the companion animal can be quickly and accurately determined using a portable terminal. Accordingly, a caregiver of the companion animal can have confidence.

According to the present invention, a current state of a companion animal is accurately determined in real time using a portable terminal so that convenience and confidence of a user can be improved.

According to the present invention, hospital information is also provided regarding a current state of a companion animal, and thus it is possible to maintain health of the companion animal by treating a disease of the companion animal at an early stage in a hospital capable of handling the disease of the companion animal.

According to the present invention, by continuously providing notification information of a companion animal to a caregiver, it is possible to induce the caregiver to visit a veterinary hospital again and prevent deviation from the veterinary hospital. According to the present invention, result data of the companion animal is shared with a linked service, and thus it is possible to find a state of the companion animal more accurately and handle the state, which gives confidence to the caregiver of the companion animal.

Effects of the present invention are not limited to those described above, and other effects which have not been described will be clearly understood by those of ordinary skill in the art from the following description.

BRIEF DESCRIPTION OF THE DRAWINGS

FIG. 7 is a sequence diagram illustrating a skin disease measurement method using a portable terminal according to an embodiment of the present invention.

MODE TO PRACTICE THE INVENTION

Figure 1:
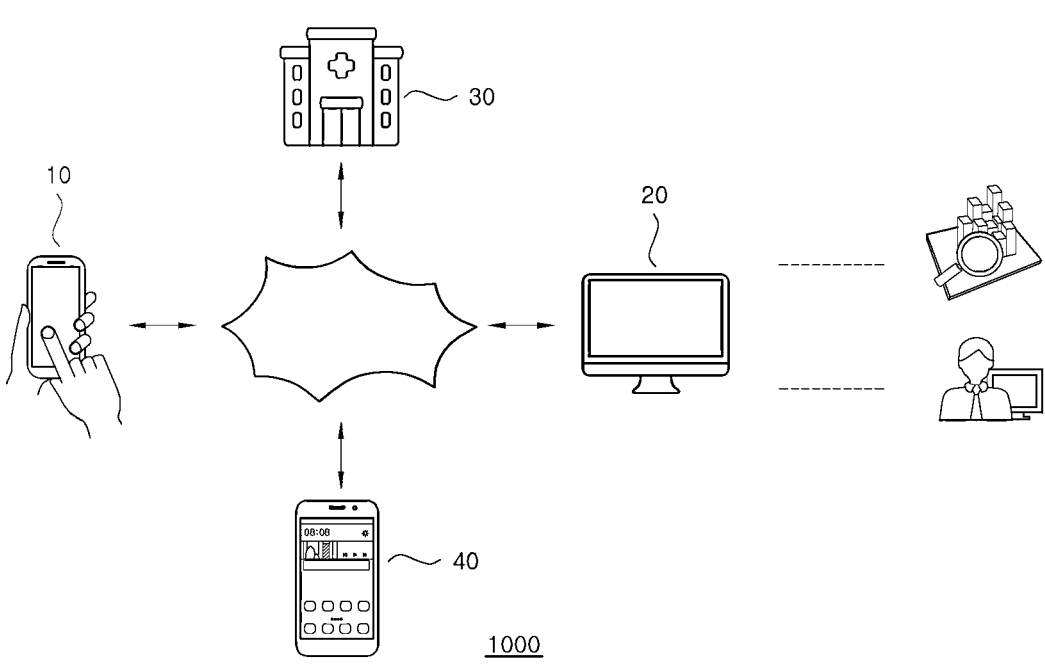
FIG. 1 is a conceptual diagram illustrating a skin disease measurement system using a portable terminal according to an embodiment of the present invention.

Advantages and features of the present invention and methods of achieving the same will become apparent with reference to embodiments described in detail below in conjunction with the accompanying drawings. However, the present invention is not limited to the embodiments disclosed below and may be implemented in various different forms. The embodiments are provided only to make the disclosure of the present invention complete and to fully convey the scope of the present invention to those of ordinary skill in the art to which the present invention pertains. The present invention is defined only by the scope of the claims.

Terminology used herein is for the purpose of describing the embodiments and is not intended to limit the present invention. As used herein, the singular forms include the plural forms as well unless the context clearly indicates otherwise. The terms "comprises" and/or "comprising" used herein do not preclude the presence or addition of one or more components other than stated components. Throughout the specification, like reference numerals refer to like components. "And/or" includes any and all combinations of one or more of the listed components. Although "first," "second," etc. may be used herein to describe various components, these components are not limited by these terms. These terms are only used to distinguish one component from another. Therefore, as used herein, a first component may be a second component within the technical spirit of the present invention.

Unless otherwise defined, all terms (including technical and scientific terms) used herein have the same meaning as commonly understood by those of ordinary skill in the art to which the present invention pertains. Also, terms defined in commonly used dictionaries are not interpreted ideally or excessively unless expressly so defined herein.

Hereinafter, embodiments of the present invention will be described in detail with reference to the accompanying drawings.

Figure 2:
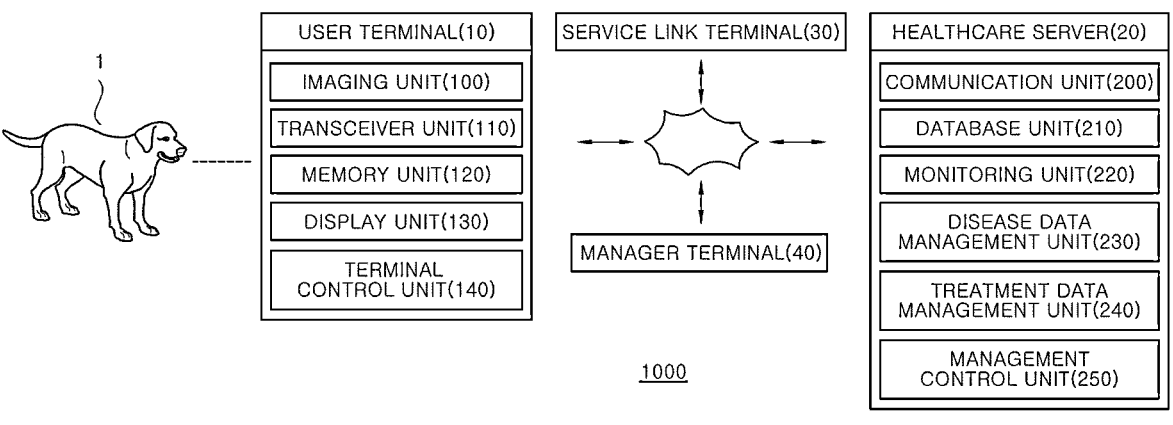
FIG. 2 is a diagram illustrating a detailed configuration of the skin disease measurement system using a portable terminal shown in FIG. 1.
Figure 3:
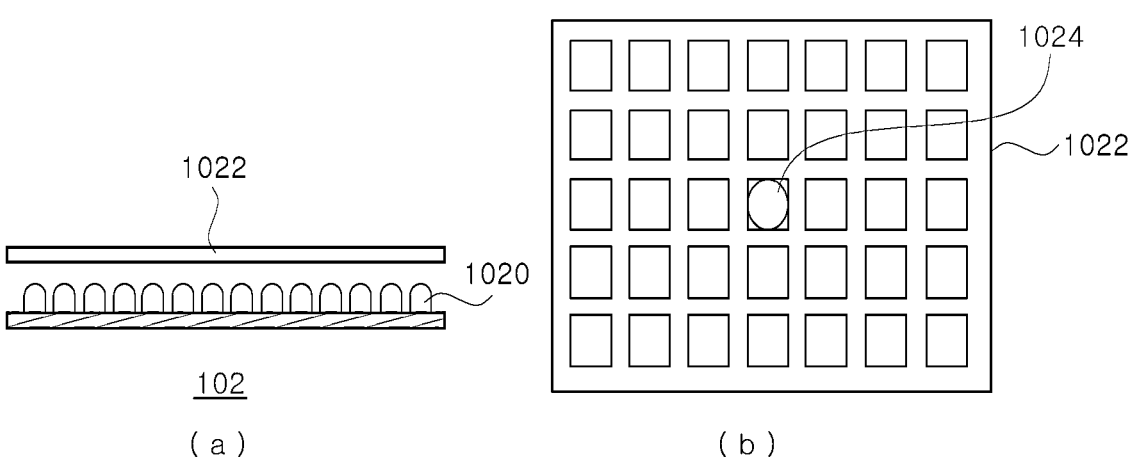
FIG. 3 is a set of tables illustrating basic skin result data for basic skin imaging information according to an embodiment of the present invention.
Figure 4:
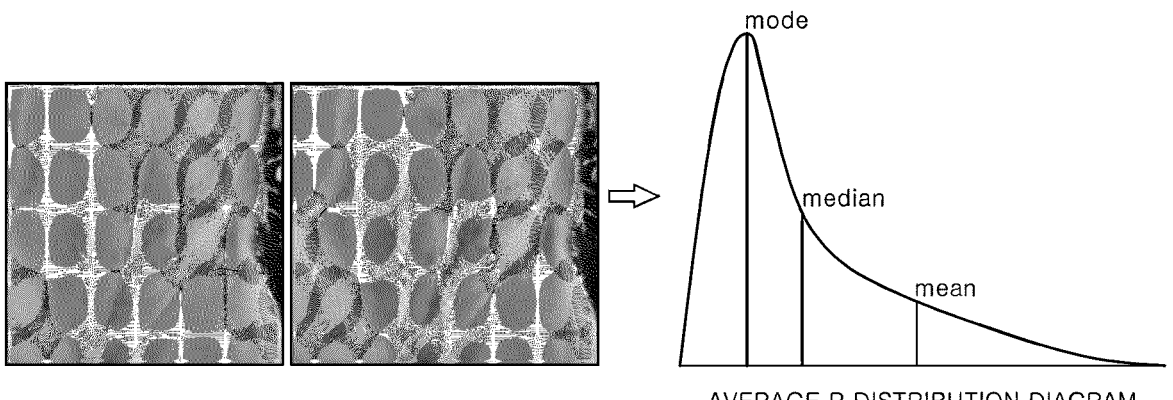
FIG. 4 is a diagram for analyzing a distribution diagram of erythema included in an image according to an embodiment of the present invention.
Figure 5:
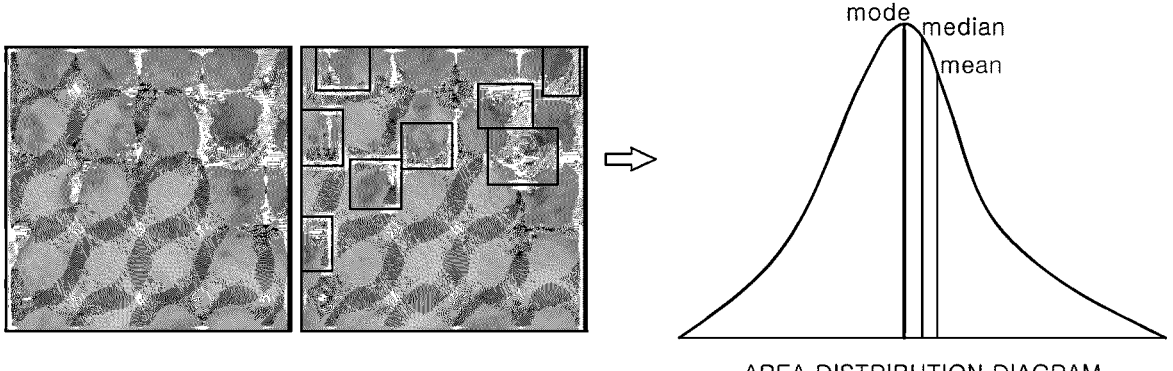
FIG. 5 is a diagram illustrating a distribution diagram of excoriation included in an image according to an embodiment of the present invention.
Figure 6:
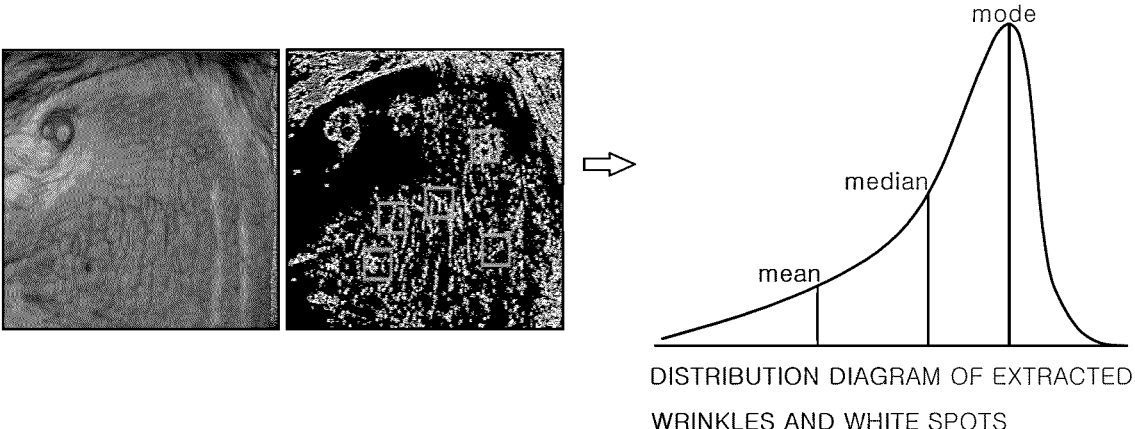
FIG. 6 is a diagram illustrating a distribution diagram of lichenification included in an image according to an embodiment of the present invention.

FIG. 1 is conceptual diagram illustrating a skin disease measurement system using a portable terminal according to an embodiment of the present invention, FIG. 2 is a diagram illustrating a detailed configuration of the skin disease measurement system using a portable terminal shown in FIG. 1, FIG. 3 is a set of tables illustrating basic skin result data for basic skin imaging information according to an embodiment of the present invention, FIG. 4 is a diagram for analyzing a distribution diagram of erythema included in an image according to an embodiment of the present invention, FIG. 5 is a diagram illustrating a distribution diagram of excoriation included in an image according to an embodiment of the present invention, and FIG. 6 is a diagram illustrating a distribution diagram of lichenification included in an image according to an embodiment of the present invention.

As shown in FIGS. 1 and 2, a skin disease measurement system 1000 using a portable terminal according to the embodiment of the present invention may include a user terminal 10, a healthcare server 20, a service link terminal 30, and a manager terminal 40. Here, the manager terminal 40 may be omitted.

The user terminal 10, the healthcare server 20, the service link terminal 30, and the manager terminal 40 may be synchronized in real time using a wireless communication network to transmit and receive data. The wireless communication network may support various long-range communication methods. For example, various communication methods, such as wireless local area network (WLAN), Digital Living Network Alliance (DLNA), Wireless Broadband (WiBro), World Interoperability for Microwave Access (WiMAX), Global System for Mobile Communications (GSM), code-division multiple access (CDMA), CDMA2000, Enhanced Voice-Data Optimized or Enhanced Voice-Data Only (EV-DO), wideband CDMA (WCDMA), High Speed Downlink Packet Access (HSDPA), High Speed Uplink Packet Access (HSUPA), the Institute of Electrical and Electronics Engineers (IEEE) 802.16, Long Term Evolution (LTE), LTE-Advanced (LTEA), Wireless Mobile Broadband Service (WMBS), Bluetooth Low Energy (BLE), ZigBee, radio frequency (RF), Long Range (LoRa), etc., may be applied. However, communication methods are not limited thereto, and various widely known wireless communication or mobile communication methods may be applied.

In the present embodiment, it is described that the skin disease measurement system 1000 is used for imaging the skin of a companion animal, particularly, a puppy, and determining severity of a skin disease, but the present invention is not limited thereto. For example, it is possible to measure not only skin diseases of various animals including vertebrates, such as mammals, birds, reptiles, amphibians, fish, etc., invertebrates, such as arthropods and mollusks, etc. living with a caregiver, a companion, or a dog owner (hereinafter, "caregiver") but also skin diseases of humans.

The user terminal 10 is a portable terminal carried by a caregiver of a companion animal 1 and may operate using an application program or application in the present disclosure. The application program may be downloaded from an external server or the healthcare server 20 through wireless communication. For example, the user terminal 10 may be one of various terminals, such as a smartphone, a personal digital assistant (PDA), a tablet, a wearable device (e.g., a smartwatch, smart glasses, a head mounted display (HMD), etc.), and various Internet of Things (IoT) terminals, but is not limited thereto.

As shown in FIG. 2, the user terminal 10 may include an imaging unit 100, a transceiver unit 110, a memory unit 120, a display unit 130, and a terminal control unit 140.

The imaging unit 100 may recognize the skin of the companion animal 1 using a camera (not shown) provided in the user terminal 10 to acquire actual skin imaging information. Here, the actual skin imaging information may include imaging information of a state in which the companion animal 1 is in need of management. For example, the actual skin imaging information may include a photograph or a video obtained by capturing a state of the skin of the companion animal 1 but is not limited thereto.

According to the embodiment, the imaging unit 100 may select a skin part of the companion animal 1 to be diagnosed and acquire actual skin imaging information of the selected skin part.

The transceiver unit 110 may transmit skin state measurement information to the healthcare server 20 and receive skin healthcare data generated on the basis of skin health standard data from the healthcare server 20. Here, the skin health standard data may be updated in real time in accordance with skin health result data.

Here, the skin state measurement information may include a photograph and a video whose brightness, visibility, etc. are automatically adjusted in consideration of surroundings, shaking, etc. on the basis of the actual skin imaging information.

Also, the skin health standard data may be data generated by matching basic skin state information of the companion animal 1 with basic skin result data.

The basic skin state information may include basic information and basic skin imaging information. The basic information may include caregiver information, abandonment information, hospital record information, a unique identification number, a dog breed, a sex, an age, a weight, a neutered state, etc. The caregiver information includes a contact number and the like, and the hospital record information may include vaccination information, medical treatment information, allergies, etc. According to the embodiment, the hospital record information may include beauty information.

The basic skin result data is data corresponding to the basic skin state information and may be data obtained by extracting an image included in the basic skin imaging information and quantifying and assessing severity of a skin disease. Here, a skin disease may be classified as erythema, excoriation, or lichenification for each diagnosis part, and severity of a skin disease may be classified into four grades (grade 0 to grade 3), but classifications and severity grades of skin diseases are not limited thereto.

The health result data may be result data obtained by quantifying severity of a skin disease of the companion animal 1 using the skin state measurement information on the basis of the skin health standard data.

According to the embodiment, the transceiver unit 110 may receive the skin health standard data from the healthcare server 20 and transmit the skin health result data to the healthcare server 20.

According to the embodiment, when the transceiver unit 110 transmits the skin state measurement information from the user terminal 10 to the healthcare server 20, the transceiver unit 110 may receive the skin health result data from the healthcare server 20.

The transceiver unit 110 may transmit or receive treatment management data. Here, the treatment management data may include recommendation information which is recommendable in accordance with a current state or a disease state of the companion animal 1, appointment management information, veterinary hospital link information, and the hospital record information but is not limited thereto.

The memory unit 120 may store data transmitted or received through the transceiver unit 110 and data for supporting various functions of the user terminal 10.

The memory unit 120 may store a plurality of application programs or applications run on the user terminal 10 and data and instructions for operations of the user terminal 10. At least some of the application programs may be downloaded from the external server through wireless communication.

The display unit 130 is a means of visually and audibly outputting a current operating state of the user terminal 10 and may include a display for outputting signs, letters, numbers, etc. on a screen in accordance with the operating state, a lamp for outputting the same with color changes or blinking, a speaker for outputting the same in the form of audio, etc.

For example, in the case of outputting the skin health result data corresponding to the skin state measurement information after measurement of the companion animal 1 is finished, the display unit 130 may display O or X regarding whether the companion animal 1 has a skin disease, blink the screen in red or green, display the guide text, such as "Everything is normal," "I recommend visiting a hospital," etc., or display actual determination data together with dictionary information. Here, the display unit 130 may output the guide text by sound so that the caregiver can accurately check a result regarding a skin disease of the companion animal 1.

Also, in the case of outputting the treatment management data, the display unit 130 may display hospital information, such as the location, the contact number, available appointment dates, etc., of a hospital corresponding to the recommendation information generated on the basis of the veterinary hospital link information together with a road view or a map or calendar, display the hospital record information including detailed treatment information, prevention information, etc., or display appointment management information including an appointment completion signal received in response to an appointment request signal of the user terminal 10 through the screen.

The terminal control unit 140 may operate the imaging unit 100 by the caregiver's manual manipulation to generate the skin state measurement information of the companion animal 1 and receive and output the skin health result data for the skin state measurement information.

Specifically, the terminal control unit 140 may automatically correct the actual skin imaging information acquired by imaging the skin of the companion animal 1, thereby generating the skin state measurement information. Here, the skin state measurement information may include actual basic information and the actual skin imaging information. The actual basic information may include the caregiver information, the hospital record information, unique identification information, the dog breed, the sex, the age, the weight, the neutered state, etc. The caregiver information may include the contact number and the like, and the hospital record information may include the vaccination information, the medical treatment information, the allergies, etc. According to the embodiment, the hospital record information may include beauty information.

The actual skin imaging information may include a photograph and a video that are generated by automatically adjusting brightness and visibility of the actual skin imaging information in consideration of surroundings, shaking, etc. Here, the photograph may be at least one, and the video may last at least 10 seconds, but the photograph and the video are not limited thereto.

In other words, the terminal control unit 140 may receive the skin health result data for the skin state measurement information regardless of time and place using the portable user terminal 10 and accurately determine a type of disease in the skin of the companion animal 1. Accordingly, it is possible to maintain health of the companion animal 1 by treating the skin disease of the companion animal 1 at an early stage, and thus convenience and reliability can be improved while diversity of caregivers is respected.

According to the embodiment, when the skin health standard data is received from the healthcare server 20, the terminal control unit 140 may generate the skin health result data by comparing and analyzing the skin state measurement information on the basis of the skin health standard data.

Also, the terminal control unit 140 may transmit or receive the treatment management data corresponding to the current state or the disease state of the companion animal 1 based on the skin health result data.

Specifically, the terminal control unit 140 may generate the appointment request signal including a hospital selection, a hospital appointment request, etc. on the basis of recommendation information which is recommended in accordance with the skin health result data on the basis of the veterinary hospital link information, transmit the appointment request signal to the healthcare server 20 or the service link terminal 30, and receive the appointment completion signal corresponding to the appointment request signal from the healthcare server 20 or the service link terminal 30. Also, the terminal control unit 140 may receive the hospital record information of the companion animal 1 from the healthcare server 20 or the service link terminal 30.

The healthcare server 20 may include a communication unit 200, a database unit 210, a monitoring unit 220, a disease data management unit 230, a treatment data management unit 240, and a management control unit 250.

The communication unit 200 may transmit the skin health result data to the user terminal 10 when the skin state measurement information is received from the user terminal 10.

According to the embodiment, when the communication unit 200 transmits the skin health standard data to the user terminal 10, the communication unit 200 may receive the skin health result data from the user terminal 10.

Also, the communication unit 200 may transmit or receive the treatment management data between the user terminal 10 and the healthcare server 20.

According to the embodiment, the communication unit 200 may transmit and receive the treatment management data between the user terminal 10 and the service link terminal 30.

The database unit 210 may store data transmitted and received between the user terminal 10 and the service link terminal 30 through the wireless communication network. Here, the skin health standard data may be updated in accordance with the skin health result data and stored in real time.

The database unit 210 may store data for supporting various functions of the healthcare server 20. The database unit 210 may store a plurality of application programs or applications run on the healthcare server 20 and data and instructions for operations of the healthcare server 20. At least some of the application programs may be downloaded from an external server through wireless communication.

Meanwhile, the basic skin state information, the skin state measurement information, the skin health result data, and the skin health standard data stored in the database unit 210 and used in the present embodiment may be implemented in mapping tables corresponding to each other but are not limited thereto.

The monitoring unit 220 may monitor an operating state of the user terminal 10, an operating state of the healthcare server 20, data transmitted and received between the user terminal 10 and the healthcare server 20, etc. through the screen. In other words, a use state of the user terminal 10 can be checked in real time, which makes the caregiver's use convenient. Accordingly, it is possible to give more confidence to the caregiver.

The disease data management unit 230 may acquire basic skin state information from a plurality of companion animals 1 and analyze the acquired basic skin state information to generate basic skin result data. Here, the basic skin state information may be information acquired from puppies at facilities, such as abandoned dog centers, shelters, etc., but is not limited thereto.

The basic skin state information may include basic information of the plurality of companion animals 1 and basic skin imaging information of various skin parts of the companion animals 1 based on the basic information. Here, the basic skin imaging information may include photographs or videos.

The basic skin imaging information may include actual skin imaging information of various skin parts such as faces, heads, abdomens, feet, chests, etc. of the companion animals 1.

The disease data management unit 230 may extract images from the basic skin imaging information on the basis of the Canine Atopic Dermatitis Extent and Severity Index (CADESI) and analyze a characteristic distribution diagram from the extracted images to quantify and assess severity of skin diseases, but a method for the disease data management unit 230 to generate basic skin result data is not limited thereto.

For example, after setting diagnosis parts from the basis skin imaging information obtained by imaging various parts, such as ears, abdomens, feet, etc., the disease data management unit 230 may extract images in accordance with the set diagnosis parts, calculate a characteristic distribution diagram using a multiple-residual concatenation (MRC) algorithm by analyzing the extracted part-specific analysis images, compare and analyze the calculated characteristic distribution diagram and symptom indices of the CADESI, quantify and assess severity of atopic dermatitis in four grades, and generate basic skin result data for the basic skin imaging information as shown in FIG. 3.

Here, the characteristic distribution diagram may be calculated by determining the distributions of erythema, excoriation, and lichenification and quantifying severity.

For example, referring to FIG. 4, severity of erythema may be assessed using an average red (R) distribution diagram calculated from the part-specific analysis images. Referring to FIG. 5, severity of excoriation may be assessed using a distribution diagram of ratios of the area of wounded parts to a total area calculated from the part-specific analysis images. Referring to FIG. 6, severity of lichenification may be assessed using a distribution diagram of the number of extracted wrinkles and white spots calculated from the part-specific analysis images.

In other words, the disease data management unit 230 may compare and analyze progression of erythema, excoriation, and lichenification in imaging information of ears, abdomens, feet, etc. with symptom indices of the CADESI and quantify and assess severity of atopic dermatitis, thereby generating the basic skin result data for the basic skin imaging information.

Meanwhile, when the basic skin imaging information is photographs, the disease data management unit 230 may generate basic skin result data for the basic skin imaging information using one photograph. Unlike this, when the basic skin imaging information is a video, the disease data management unit 230 may determine normal images in the video through a filtering operation and extract at least 10 images to generate basic skin result data for the basic skin imaging information. Here, a Laplace filter may be used for filtering so that normal images are acquired. However, the filtering operation is not limited thereto.

The treatment data management unit 240 may manage the treatment management data transmitted and received between the user terminal 10 and the service link terminal 30 on the basis of the skin health result data. Here, the treatment management data may include recommendation information which is recommendable in accordance with a current state or a disease state of the companion animal 1, appointment management information, veterinary hospital link information, and hospital record information.

For example, when treatment is necessary in accordance with actual diagnosis data, the treatment data management unit 240 may provide recommendation information generated on the basis of the hospital information to the user terminal 10. Here, the recommendation information may be information for recommending hospital information corresponding to the skin health result data using the veterinary hospital link information generated on the basis of the hospital information received from the service link terminal 30.

Also, the treatment data management unit 240 may transmit and receive appointment management information between the user terminal 10 and the service link terminal 30.

For example, the treatment data management unit 240 may transmit the appointment request signal received from the user terminal 10 to the service link terminal 30 and transmit the appointment completion signal generated in response to the appointment request signal by the service link terminal 30 to the user terminal 10.

Also, the treatment data management unit 240 may transmit the hospital record information to the user terminal 10. Here, the treatment data management unit 240 may receive the hospital record information from the service link terminal 30.

For example, after treatment of the companion animal 1 is completed, the treatment data management unit 240 may transmit hospital record information including detailed treatment information to the user terminal 10. In general, the treatment data management unit 240 may transmit hospital record information including prevention information or beauty information to the user terminal 10. Also, the treatment data management unit 240 may transmit notification information about the companion animal 1 to the user terminal 10. Here, the notification information is information generated by the service link terminal 30 and may be, but is not limited to, notification information about treatment or beauty of the companion animal 1.

According to the embodiment, the treatment data management unit 240 may share the hospital record information with another server.

The management control unit 250 may generate the skin health standard data by matching the basic skin state information with the basic skin result data using deep learning. In the present embodiment, it has been described that deep learning is used. However, the present invention is not limited thereto, and a machine learning technique, such as random forest, support vector machine, etc., may be used. Here, the management control unit 250 may update the skin health standard data in real time in accordance with the skin health result data.

Specifically, the management control unit 250 may repeatedly learn the basic skin state information and the basic skin result data on the basis of a convolutional neural network (CNN) algorithm and verify suitability to generate the skin health standard data. Here, a process of verifying the skin health standard data may involve, but is not limited to, veterinarians and research staff of a committed research institution, for example, at least three specialists, doing cross validation on suitability.

Also, when the skin state measurement information is received from the user terminal 10, the management control unit 250 may generate the skin health result data on the basis of the skin health standard data.

Specifically, the management control unit 250 may extract an actual analysis image from each set diagnosis part by preprocessing the photograph and/or the video included in the skin state measurement information, calculate an actual characteristic distribution diagram using the MRC algorithm by analyzing the extracted part-specific actual analysis images, and generate the skin health result data in which severity of skin diseases is quantified by comparing and analyzing the calculated actual characteristic distribution diagram on the basis of the skin health standard data. Here, skin diseases may be classified as erythema, excoriation, and lichenification for about 20 diagnosis parts, and severity of a skin disease may be classified into four grades (grade 0 to grade 3), but classifications and severity grades of skin diseases are not limited thereto.

In other words, the management control unit 250 may extract an analyzable actual analysis image from the photograph or the video included in the actual skin imaging information in consideration of surroundings, shaking, etc., automatically correct brightness, visibility, etc. of the extracted part-specific actual analysis image, and compare and analyze the actual characteristic distribution diagram and the skin health standard data to generate the skin health result data including severity of the skin diseases.

Meanwhile, when the actual skin imaging information is photographs, the management control unit 250 may generate skin health result data corresponding to the skin state measurement information on the basis of the skin health standard data using one photograph. Unlike this, when the actual skin imaging information is a video, the management control unit 250 may determine normal images in the video through a filtering operation and extract at least 10 images to generate skin health result data corresponding to the skin state measurement information on the basis of the skin health standard data. Here, a Laplace filter may be used for filtering so that normal images are acquired by filtering shaking of images included in the video. However, the filtering operation is not limited thereto.

According to the embodiment, when the management control unit 250 transmits the skin health standard data to the user terminal 10, the management control unit 250 may receive the skin health result data corresponding to the skin state measurement data of the companion animal 1.

According to the embodiment, the management control unit 250 may transmit or receive advertising information together with data transmitted to or received from the user terminal 10, the service link terminal 30, and/or the manager terminal 40. Accordingly, advertising revenue can be generated to support facilities such as abandoned dog centers, shelters, etc.

The healthcare server 20 having the above structure may automatically extract a diagnosis part from skin state measurement information acquired through the user terminal 10 on the basis of skin health standard data which is verified by repeatedly learning basic skin result data generated in accordance with basic skin state information acquired from the plurality of companion animals 1, and compare and analyze extracted part-specific actual analysis images, thereby generating skin health result data in which severity of a skin disease is classified into four grades (grade 0 to grade 3). Accordingly, it is possible to solve problems including unnecessary hospital visits, negligence, etc. which may be caused when the state of the companion animal 1 is determined only visually.

Also, the healthcare server 20 provides recommendation information to the user terminal 10 in accordance with the current state or the disease state of the companion animal 1 so that the companion animal 1 can be quickly and accurately managed.

The healthcare server 20 may be implemented as a hardware circuit (e.g., a complementary metal-oxide semiconductor (CMOS)-based logic circuit), firmware, software, or a combination thereof. For example, the healthcare server 20 may be implemented in the form of one of various electrical structures using transistors, logic gates, and electronic circuitry.

The service link terminal 30 is a plurality of veterinary hospitals for managing health of the companion animal 1 and examining the companion animal 1 and may examine the companion animal 1 more quickly using the skin health result data.

The service link terminal 30 may share the hospital record information with the user terminal 10, the healthcare server 20, and an additional server.

The service link terminal 30 may provide the hospital information and notification information to the user terminal 10 and/or the healthcare server 20.

According to the embodiment, the service link terminal 30 may include additional facilities such as an abandoned dog center, a shelter, etc.

The manager terminal 40 is a terminal carried by a manager and may be synchronized in real time with the user terminal 10, the healthcare server 20, and the service link terminal 30 using the wireless communication network to transmit and receive data. Here, the manager terminal 40 may transmit and receive data using an application program or an application.

The manager terminal 40 may learn the skin health standard data received from the healthcare server 20 and analyze the skin state measurement information received from the user terminal 10, thereby generating the skin health result data.

According to the embodiment, when the skin state measurement information is received from the user terminal, the manager terminal 40 may compare and analyze the skin state measurement information on the basis of the skin health standard data, thereby generating the skin health result data.

According to the embodiment, when the skin health result data is generated by the user terminal 10, the manager terminal 40 may receive the skin health result data from the user terminal 10 and transmit the skin health result data to the healthcare server 20. Also, when the skin health result data is generated by the healthcare server 20, the manager terminal 40 may receive the skin health result data from the healthcare server 20 and transmit the skin health result data to the user terminal 10.

According to the embodiment, the manager terminal 40 may transmit or receive the treatment management data corresponding to the current state or the disease state of the companion animal 1 based on the skin health result data to or from at least one of the user terminal 10, the healthcare server 20, and the service link terminal 30.

The manager terminal 40 may be one of various portable electronic communication devices that support communication with the user terminal 10, the healthcare server 20, and the service link terminal 30. For example, the manager terminal 40 may be one of various terminals, such as a smartphone, a PDA, a tablet, a wearable device (e.g., a smartwatch, smart glasses, an HMD, etc.), and various IoT terminals, but is not limited thereto.

The skin disease measurement system using a portable terminal and having the above structure according to the embodiment of the present invention operates as follows. FIG. 7 is a sequence diagram illustrating a skin disease measurement method using a portable terminal according to an embodiment of the present invention, FIG. 8 is a detailed flowchart illustrating a method of generating skin health standard data shown in FIG. 7, and FIG. 9 is a set of views illustrating skin health result data shown in FIG. 7.

First, in the embodiment of the present invention, an image of the skin of a puppy among the companion animals 1 is extracted to determine and quantify severity of atopy, but the present invention is not limited thereto.

As shown in FIG. 7, the healthcare server 20 may generate skin health standard data (S10).

Figure 8:
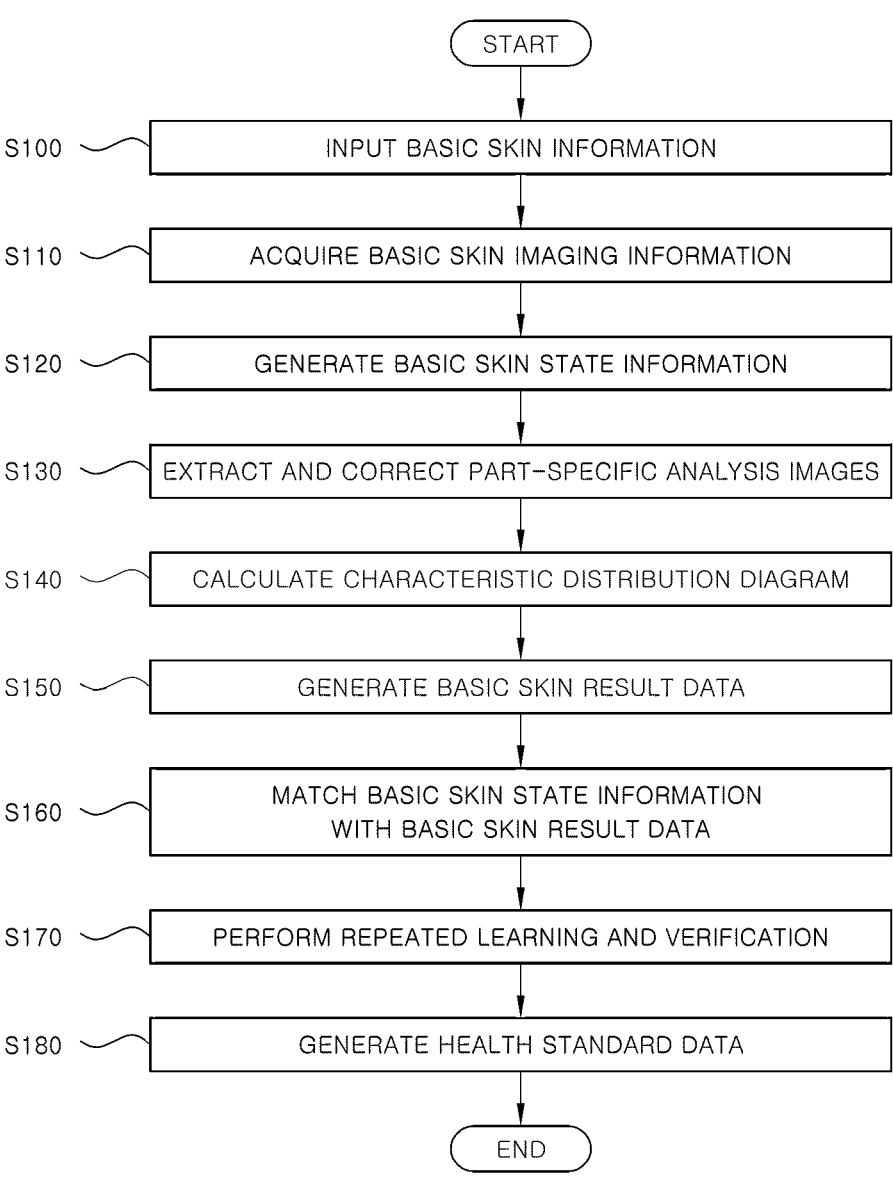
FIG. 8 is a detailed flowchart illustrating a method of generating skin health standard data shown in FIG. 7.
Figure 9:
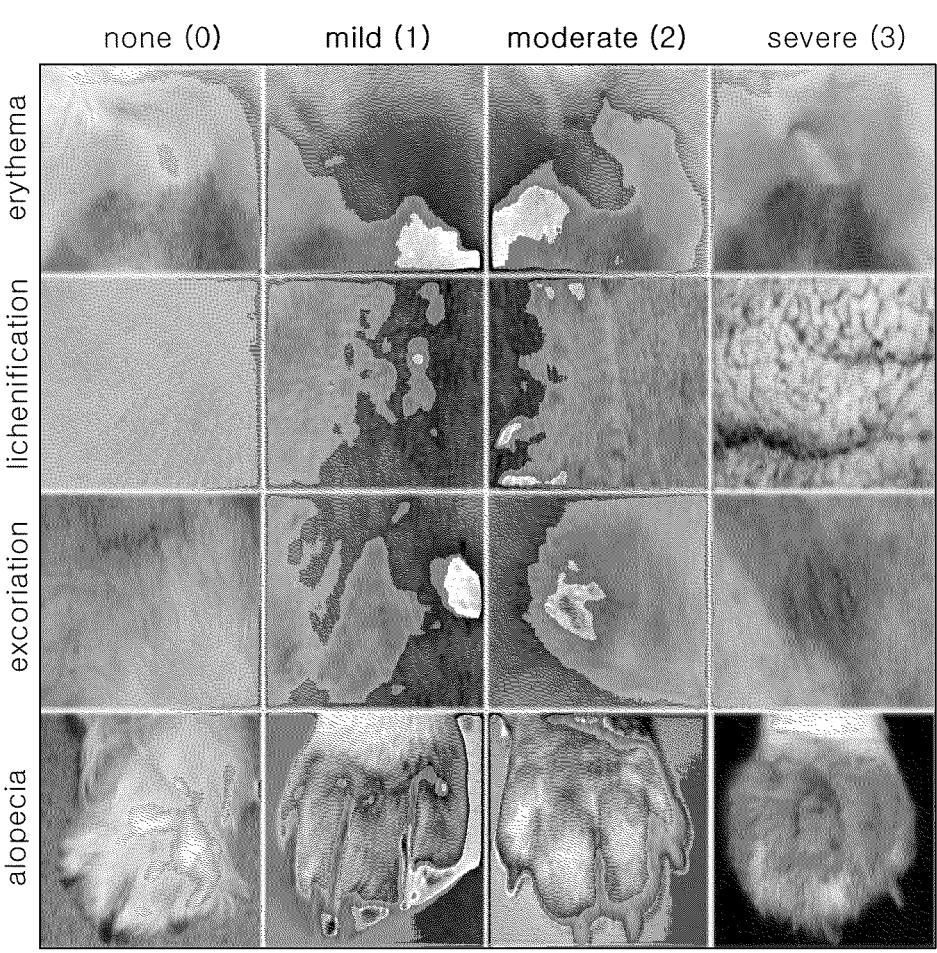
FIG. 9 is a set of views illustrating skin health result data shown in FIG. 7.

Specifically, referring to FIG. 8, the healthcare server 20 may acquire basic information from a plurality of companion animals 1 (S100). Here, the basic information may include caregiver information, abandonment information, hospital record information, unique identification numbers, dog breeds, sexes, ages, weights, neutered statuses, etc. but is not limited thereto.

For example, the disease data management unit 230 may receive the basic information of the companion animals 1 using a separate mobile terminal.

Subsequently, the healthcare server 20 may image the skin of the companion animals 1 on the basis of the basic information (S110).

For example, the disease data management unit 230 may acquire basic skin imaging information by imaging the skin of the abdomens, the ears, and the feet of the companion animals 1.

In the present embodiment, parts to be imaged may be set to abdomens, ears, and feet among body parts of the companion animals 1, but parts to be imaged are not limited thereto. Parts to be imaged may be selected from various body parts such as faces, chests, backs, tails, etc.

Subsequently, the healthcare server 20 may generate basic skin state information using the basic information and the basic skin imaging information (S120). Here, the basic skin imaging information may include at least one photograph and a video lasting at least 10 seconds.

Subsequently, the healthcare server 20 may extract analysis images which are analyzable part by part from the basic skin imaging information and correct the analysis images (S130).

Specifically, when imaging information included in the basic skin imaging information is photographs, the healthcare server 20 may verify whether the photographs are analyzable images.

For example, the disease data management unit 230 may extract the analysis images which are analyzable part by part in consideration of surroundings, shaking, etc. Here, the extracted analysis images may be corrected.

Meanwhile, when the imaging information included in the basic skin imaging information is a video, the healthcare server 20 may extract normal images by filtering shaking of images included in the video. For example, the disease data management unit 230 may determine normal images from the video using a Laplace filter through a filtering operation, thereby extracting at least 10 images.

Subsequently, the healthcare server 20 may calculate a characteristic distribution diagram for the part-specific analysis images (S140).

For example, the disease data management unit 230 may calculate characteristic distribution diagrams for erythema, excoriation, and lichenification from the part-specific analysis images through quantification.

Subsequently, the healthcare server 20 may compare and analyze progression of erythema, excoriation, and lichenification with symptom indices of the CADESI to generate basic skin result data corresponding to the basic skin state information (S150).

Subsequently, the healthcare server 20 may match the basic skin state information with the basic skin result data (S160) and repeatedly learn the basic skin state information and the basic skin result data on the basis of a CNN algorithm to verify suitability and generate skin health standard data (S170 and S180).

After that, when a caregiver requests a diagnosis of a current state or a disease state of a companion animal 1, the user terminal 10 may acquire actual skin imaging information of a body part of the companion animal 1 (S12).

In the present embodiment, it is described that actual skin imaging information of the ears, the abdomen, and the feet of the companion animal 1 is acquired, but the present invention is not limited thereto.

Subsequently, the user terminal 10 may receive actual basic information and generate skin state measurement information using the actual basic information and the actual skin imaging information (S14).

Subsequently, the healthcare server 20 may generate skin health result data corresponding to the skin state measurement information on the basis of the skin health standard data (S16).

Specifically, the management control unit 250 may extract actual part-specific actual analysis images by preprocessing a photograph and/or a video included in the skin state measurement information, calculate a characteristic distribution diagram for the actual analysis images using an MRC algorithm by analyzing the actual analysis images, and generate skin health result data by comparing and analyzing the characteristic distribution diagram with the skin health standard data obtained by quantifying severity of atopic dermatitis (see FIG. 9).

Subsequently, the user terminal 10 may receive the skin health result data corresponding to the skin state measurement information from the healthcare server 20 (S18).

Subsequently, the service link terminal 30 may provide hospital information on the basis of the skin health standard data (S20).

Here, the operation of providing the hospital information may be performed in advance.

Subsequently, the healthcare server 20 may generate veterinary hospital link information on the basis of the hospital information (S22).

Here, the operation of generating veterinary hospital link information may be performed in advance.

Subsequently, the healthcare server 20 may generate recommendation information corresponding to the skin health result data on the basis of the veterinary hospital link information and transmit the recommendation information to the user terminal 10 (S24).

Subsequently, the healthcare server 20 may generate appointment management information (S26).

For example, the healthcare server 20 may receive an appointment request signal generated in accordance with customized information from the user terminal 10, receive appointment management information corresponding to the appointment request signal from the service link terminal 30, and transmit the appointment management information to the user terminal 10.

Subsequently, the service link terminal 30 may generate and share hospital record information including detailed treatment information of the companion animal 1 (S28).

Here, the hospital record information may be transmitted to the user terminal 10 and the healthcare server 20.

Finally, the healthcare server 20 may update the skin health standard data in real time in accordance with the skin health result data (S30).

Operations of a method or algorithm described in connection with embodiments of the present invention may be directly implemented by hardware, implemented as a software module which is executed by hardware, or implemented by a combination thereof. The software module may be on a random access memory (RAM), a read only memory (ROM), an erasable programmable ROM (EPROM), an electrically erasable programmable ROM (EEPROM), a flash memory, a hard disk, a detachable disk, a compact disc (CD)-ROM, or any form of computer-readable recording medium well known in the technical field to which the present invention pertains.

Although embodiments of the present invention have been described with reference to the accompanying drawings, those of ordinary skill in the art to which the present invention pertains should understand that the present invention can be implemented in other specific forms without changing the technical spirit or essential characteristics thereof. Therefore, it should be understood that the above-described embodiments are illustrative in all aspects and not restrictive.

The invention claimed is:

1. A skin disease measurement method using a portable terminal, the skin disease measurement method comprising:

matching, by a healthcare server, basic skin state information with basic skin result data to generate skin health standard data;

receiving, by the healthcare server, skin state measurement information for a skin disease of a test subject from a user terminal; and comparing and analyzing, by the healthcare server, the skin state measurement information on the basis of the skin health standard data to generate skin health result data, wherein the generation of the skin health standard data includes preprocessing, by the healthcare server, images included in basic skin imaging information included in the basic skin state information;

extracting, by the healthcare server, part-specific analysis images from the preprocessed images;

analyzing, by the healthcare server, a characteristic distribution diagram from the part-specific analysis images; and quantifying, by the healthcare server, and assessing severity of the skin disease of the test subject using the analyzed characteristic distribution diagram, wherein the analyzing of the characteristic distribution diagram comprises analyzing, by the healthcare server, a characteristic distribution diagram for at least one skin disease among erythema, excoriation, and lichenification from the part-specific analysis images using a multiple-residual concatenation (MRC) algorithm.

2. The skin disease measurement method of claim 1, wherein the healthcare server assesses severity of erythema using an average red (R) distribution diagram calculated from the part-specific analysis images, assesses severity of excoriation using a distribution diagram of ratios of an area of wounded parts to a total area calculated from the part-specific analysis images, and assesses severity of lichenification using a distribution diagram of a number of extracted wrinkles and white spots calculated from the part-specific analysis images.

3. The skin disease measurement method of claim 1, wherein the generation of the skin health standard data comprises repeatedly learning, by the healthcare server, the basic skin result data corresponding to the basic skin state information to verify the basic skin result data.

4. The skin disease measurement method of claim 1, wherein the generation of the skin health result data comprises:

extracting, by the healthcare server, part-specific actual analysis images from actual skin imaging information included in the skin state measurement information and correcting the part-specific actual analysis images;

analyzing, by the healthcare server, a characteristic distribution diagram from the part-specific actual analysis images; and comparing, by the healthcare server, and analyzing the characteristic distribution diagram and the skin health standard data and quantifying and assessing severity of the skin disease of the test subject to generate the skin health result data.

5. The skin disease measurement method of claim 1, comprising transmitting or receiving, by the healthcare server, treatment management data generated in accordance with the skin health result data to or from the user terminal.

6. The skin disease measurement method of claim 5, comprising transmitting and receiving, by the healthcare server, the treatment management data between the user terminal and a service link terminal.

7. The skin disease measurement method of claim 1, further comprising updating, by the healthcare server, the skin health standard data in real time in accordance with the skin health result data.

8. A skin disease management method using a portable terminal, the skin disease management method comprising:

generating, by a healthcare server, skin healthcare data corresponding to skin state measurement information for a skin disease of a test subject received from a user terminal;

17 sharing, by the healthcare server, the skin healthcare data with a service link terminal;

transmitting, by the healthcare server, recommendation information generated in accordance with the skin healthcare data on the basis of hospital information received from the service link terminal to the user terminal;

transmitting and receiving, by the healthcare server, appointment management information between the user terminal and the service link terminal; and generating, by the service link terminal, treatment management data in accordance with the skin health result data, wherein the service link terminal periodically transmits notification information about the test subject to the user terminal, wherein the healthcare server analyzes a characteristic distribution diagram for at least one skin disease among erythema, excoriation, and lichenification from the part-specific analysis images using a multiple-residual concatenation (MRC) algorithm.

9. A skin disease measurement system using a portable terminal, the skin disease measurement system comprising:

a user terminal configured to generate skin state measurement information including actual skin imaging information of a skin disease acquired from a test subject; and a healthcare server configured to learn skin health standard data generated by matching basic skin state information with basic skin result data, analyze the skin state measurement information, quantify severity of the skin disease of the test subject, and generate skin health result data, wherein the healthcare server generates the skin health result data by analyzing a characteristic distribution diagram for at least one skin disease among erythema, excoriation, and lichenification using part-specific analysis images extracted from the actual skin imaging information, wherein the healthcare server analyzes the characteristic distribution diagram for the at least one skin disease among the erythema, the excoriation, and the lichenification from the part-specific analysis images using a multiple-residual concatenation (MRC) algorithm.

10. The skin disease measurement system of claim 9, comprising a service link terminal configured to share treatment management data generated in accordance with the skin health result data.

11. The skin disease measurement system of claim 9, further comprising a manager terminal configured to receive the skin state measurement information from the user terminal, repeatedly learn the skin health standard data when the skin health standard data is received from the healthcare server, and generate the skin health result data corresponding to the skin state measurement information.

*   *   *   *   *